United States Patent [19]
Yates et al.

[11] Patent Number: 5,755,717
[45] Date of Patent: May 26, 1998

[54] ELECTROSURGICAL CLAMPING DEVICE WITH IMPROVED COAGULATION FEEDBACK

[75] Inventors: David C. Yates, West Chester; William D. Fox, New Richmond, both of Ohio

[73] Assignee: Ethicon Endo-Surgery, Inc., Cincinnati, Ohio

[21] Appl. No.: 586,077

[22] Filed: Jan. 16, 1996

[51] Int. Cl.$^6$ .................................................. A61B 17/36
[52] U.S. Cl. .......................... 606/51; 606/41; 606/45
[58] Field of Search .......................... 606/41, 42, 45–52, 606/205–208

[56] References Cited

U.S. PATENT DOCUMENTS

| | | | |
|---|---|---|---|
| 2,068,721 | 1/1937 | Wappler et al. | |
| 4,655,216 | 4/1987 | Tischer | |
| 5,151,102 | 9/1992 | Kamiyama et al. | 606/52 |
| 5,190,541 | 3/1993 | Abele et al. | 606/46 |
| 5,267,998 | 12/1993 | Hagen | 606/45 |
| 5,389,098 | 2/1995 | Tsuruta et al. | |
| 5,403,312 | 4/1995 | Yates et al. | 606/50 |
| 5,443,463 | 8/1995 | Stern et al. | 606/51 |
| 5,445,638 | 8/1995 | Rydell et al. | |
| 5,458,598 | 10/1995 | Feinberg et al. | |
| 5,573,535 | 11/1996 | Viklund | 606/52 |
| 5,599,350 | 2/1997 | Schulze et al. | 606/51 |

*Primary Examiner*—Michael Peffley
*Attorney, Agent, or Firm*—Bernard Shay

[57] ABSTRACT

An electrosurgical hemostatic instrument is provided in which the coagulation status of tissue engaged by two elements delivering electrosurgical energy to tissue may be observed. A preferred embodiment of the invention provides a bipolar endoscopic clamping, coagulation and cutting device. The end effector of the device includes interleaved winged electrodes which act to support the tissue and to provide visual access to the tissue as it is being treated. The winged electrodes are interspersed along the outside of the end effector.

12 Claims, 6 Drawing Sheets

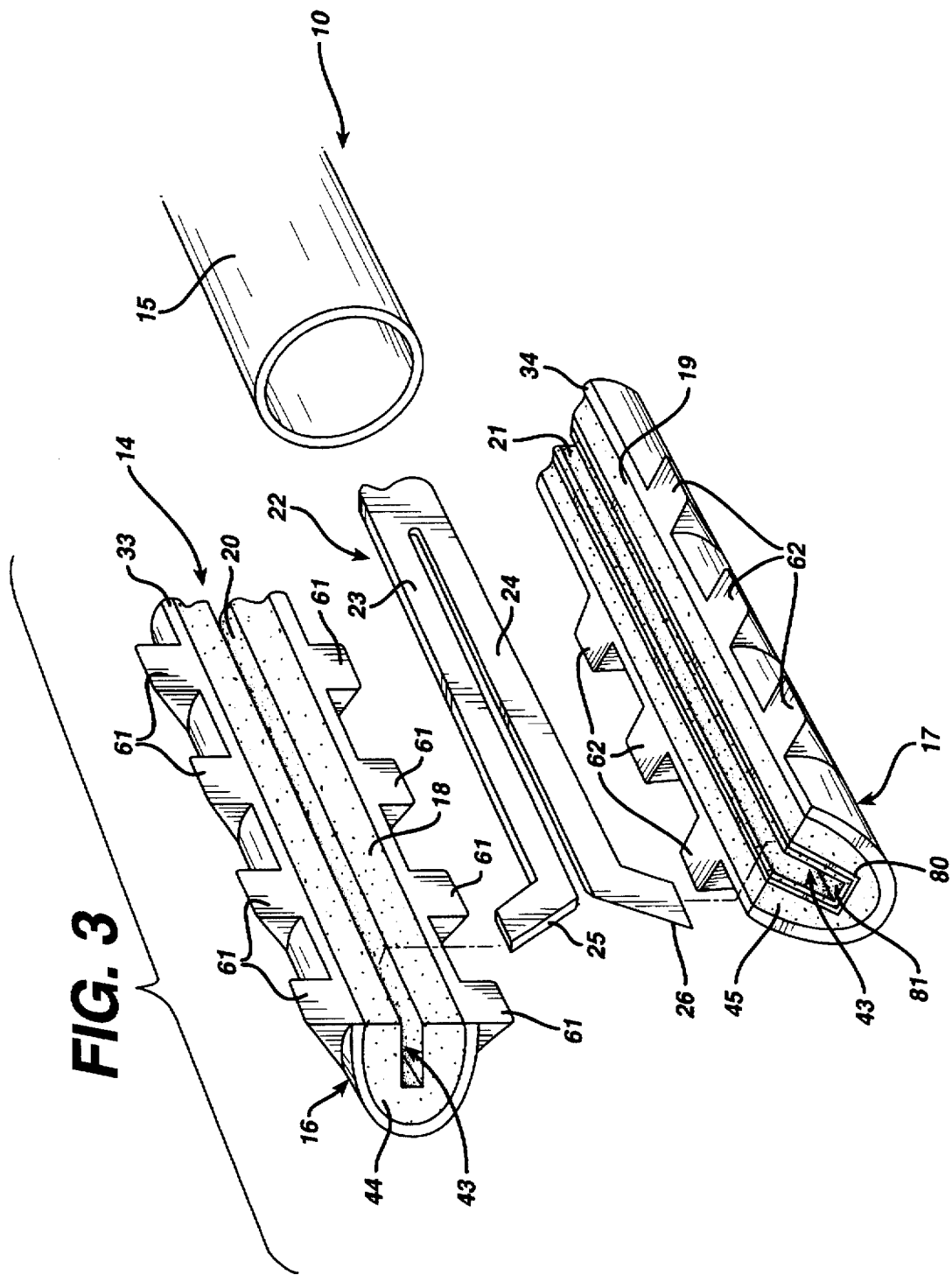

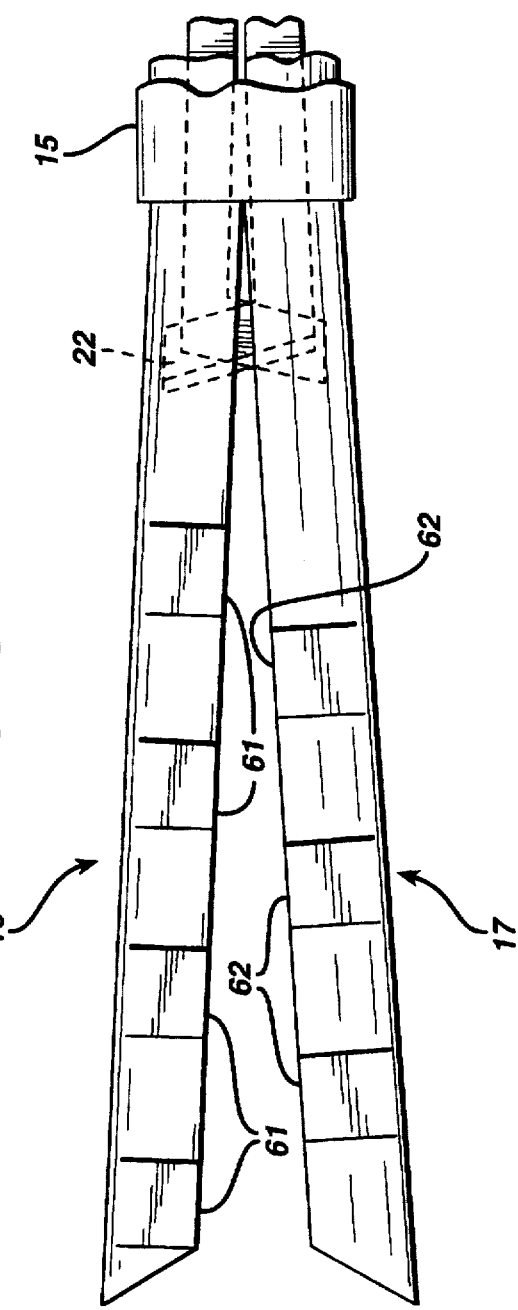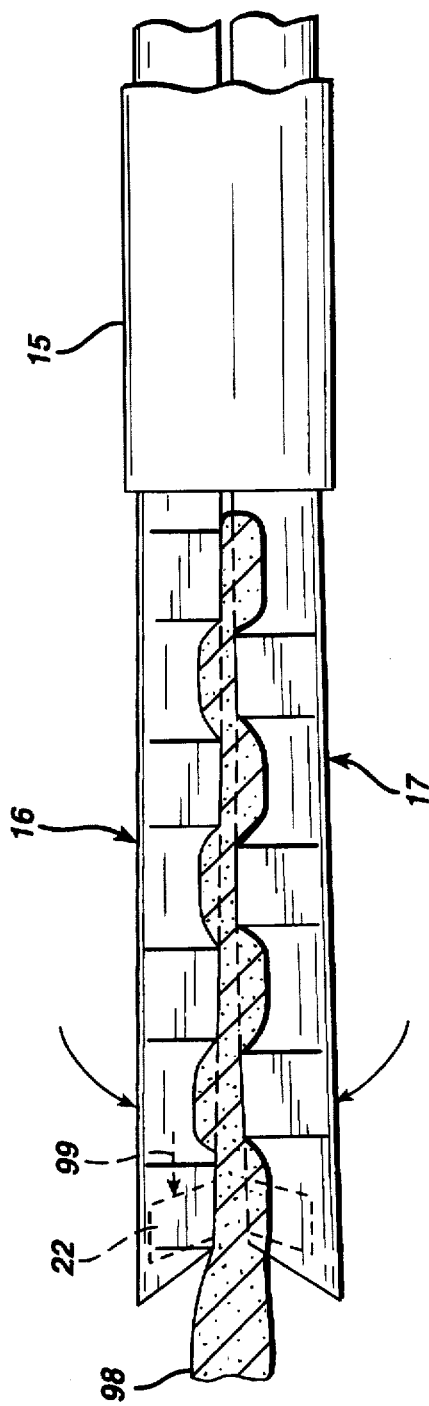

ELECTROSURGICAL CLAMPING DEVICE WITH IMPROVED COAGULATION FEEDBACK

FIELD OF THE INVENTION

The present invention relates to an electrosurgical hemostatic grasping, cutting, clamping or forceps type device, and, in particular, to an electrosurgical device including wing electrodes for enhanced visual feedback or monitoring of tissue being electrosurgically treated by the device.

BACKGROUND OF THE INVENTION

In many surgical procedures tissue is electrosurgically treated by passing an electrical current through the to tissue heat the tissue. Heating tissue generally acts to coagulate the blood and other bodily fluids in the tissue, sealing the blood vessels and improving hemostasis. Heating the tissue to an appropriate temperature may also cauterize or desiccate the tissue. Using an electrosurgical instrument, heat is generated in the tissue by inducing electrical current to flow between electrodes which are connected to an external generator. In monopolar electrosurgical instruments, a first, treatment electrode is associated with the electrosurgical instrument and a second, return electrode is attached externally to the patient. In bipolar electrosurgical instruments, both the treatment and return electrodes are located in the electrosurgical instrument and, more particularly in the end effector of the instrument and more.

Grasping type bipolar electrosurgical instruments, such as bipolar forceps, may be used to electrosurgically treat tissue in various procedures. Bipolar forceps include two opposing jaws wherein each jaw includes at least one electrode. The jaws are used to grasp tissue and electrical current flows from one electrode to the other through the grasped tissue. However, since the flow of electrical current and the heat generated by the electrical current is not confined to tissue directly between the electrodes, the effects of the current may be seen in tissue outside the forceps. These effects, which may include coagulation, cauterization and desiccation may be referred to as thermal spread. Thermal spread may be detrimental since it is generally desirable not to electrically treat tissue outside the end effector of the instrument. However, in certain instances a limited amount of thermal spread may be desirable. For example, where it is difficult to see the tissue being treated, the surgeon may rely on the color and size of the thermal spread as a visual indication of the status of the tissue in the end effector.

Thus, the thermal spread may be used by the physician as visual feed back to determine when to stop treating the tissue.

In some earlier instruments, the operator has relied upon thermal spread as an indication of the status of the treated tissue. U.S. Pat. No. 5,403,312, illustrates, in one embodiment, a clamping and coagulating device in which most of the tissue being treated by the end effector of the device is not visible to the user. The electrodes in the preferred embodiment of this device are offset from each other with respect to the tissue grasping surfaces to reduce the likelihood of arcing or shorting. Thus, in this device it may be difficult to visualize changes in the color or texture of the tissue in the end effector as the tissue is being electrosurgically treated. Alternatively, other instruments have provided enhanced visualization in other ways. U.S. patent application Ser. No. 08/415,957, filed on Apr. 3, 1995 and U.S. patent application Ser. No. 08/096,154, filed on Jul. 22, 1993, illustrate a number of clamping and coagulating instruments wherein tissue being coagulated or tissue immediately adjacent thereto may be observed during the coagulation process. In particular, in one instrument, windows in the end effector are used to view tissue grasped by the end effector. In another instrument, one of the jaws of the end effector extends distally beyond the other jaw to provide a stepped area or zone of enhanced visualization. In another instrument, notches or recesses are provided in the jaw surface adjacent the tissue grasping surface to provide visual access to the tissue during coagulation.

Thus, in many electrosurgical devices, tissue is grasped between the jaws of the end effector, limiting visual access to the tissue as it is treated. This limited access may, at times, present a problem for surgeons who rely upon the color and visual texture of the treated tissue as a visual indication of the status of the tissue. One way to overcome this problem is to rely upon the thermal spread as a visual indication of the status of the tissue being treated. However, it is not always possible to rely upon thermal spread, for example where space is limited and adjacent tissue structures must be protected it may be desirable to limit thermal spread. Alternatively, access ports such as holes, slots or recesses may be formed in the end effector to enhance visual access to the treated tissue. While effective in many circumstances, such access ports are not always positioned to provide the user with adequate visual access to the treated tissue, particularly where the end effector is being used in tight spaces or at odd angles. Thus, it would be beneficial to design an end effector wherein the electrodes are arranged such that the user has substantially improved visual access to the treated tissue, eliminating or substantially reducing the necessity of relying on thermal spread as an indication of tissue status.

SUMMARY OF THE INVENTION

In an electrosurgical instrument according to the present invention, the end effector comprises first and second tissue grasping elements which include first and second tissue grasping surfaces. Tissue is grasped between the tissue grasping surfaces when the tissue grasping elements move from an open position to a closed position. In one embodiment of the present invention, at least one of the tissue grasping surfaces includes at least one internal electrode and at least one of the tissue grasping surfaces includes at least one wing electrode. In this embodiment, the electrodes are arranged such that tissue grasped between the first and second tissue grasping elements provides at least a portion of an electrical path between the wing electrode and the internal electrode.

In a further embodiment of the present invention, a first one of the tissue grasping surfaces includes at least one wing electrode and a second one of the tissue grasping surfaces includes at least one wing electrode. In this embodiment, the electrodes are arranged such that tissue situated between the wing electrodes provides at least a portion of an electrical path between the wing electrodes.

In a further embodiment of the present invention, both of the grasping elements includes at least one internal electrode and at least one wing electrode. In this embodiment, the wing electrode is separated from the bar electrode by an insulation region which may form at least a portion of the tissue grasping surface. Alternatively, in this embodiment, both grasping elements include at least one internal electrode and at least one wing electrode wherein the bar and wing electrodes on each grasping element may be separated by an insulation region which insulation region may form at least a portion of the tissue grasping surface.

In a further embodiment of the present invention, the wing electrode may comprise one or more electrically conductive regions which protrude from the edges of at least one of the tissue grasping elements. In this embodiment, the wing electrodes include at least one electrically conductive contact surface arranged to contact tissue when the tissue is held between the tissue grasping elements.

In a further embodiment of the present invention, the internal electrodes may be electrically isolated from the winged electrodes. In this embodiment, the internal electrodes associated with a first tissue grasping element are electrically connected to the winged electrodes associated with that first tissue grasping element. In a further embodiment of the present invention, the internal electrode of a first tissue grasping element may be electrically connected to the winged electrodes of a second tissue grasping element.

In a further embodiment of the present invention, the internal electrode may comprise a bar electrode. In this embodiment, the internal electrode is embedded in at least one of the tissue grasping faces and may be oriented along the proximal to distal axis of the device

BRIEF DESCRIPTION OF THE DRAWING

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 3 is a perspective break away view of the end effector of the surgical instrument illustrated in FIG. 1.

FIG. 4 is a side view of an end effector including winged electrodes according to the present invention.

FIG. 5 is a side view of the end effector illustrated in FIG. 4 with tissue grasped between the jaws of the instrument.

DETAILED DESCRIPTION OF THE INVENTION

Figure 1:
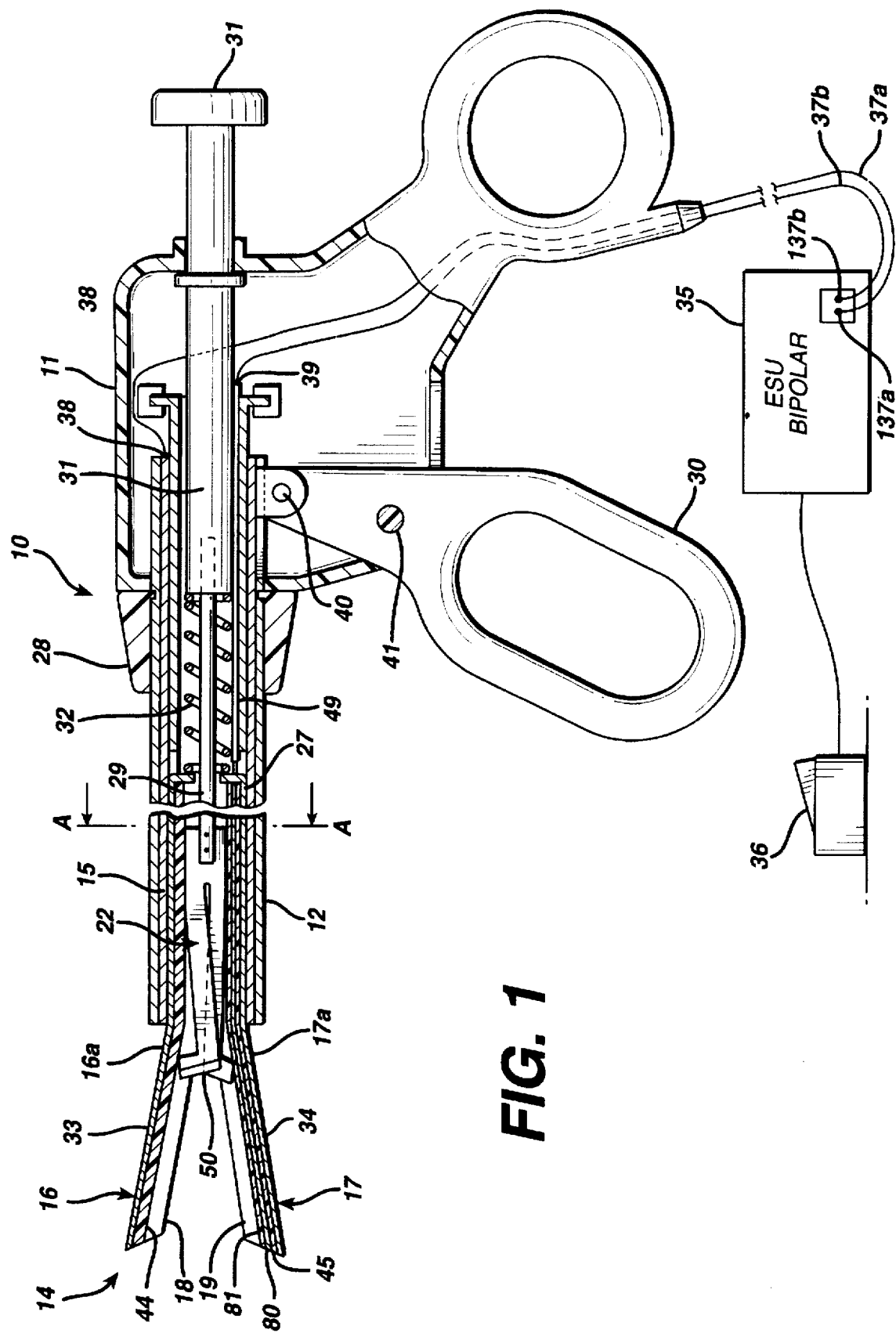
FIG. 1 is an elevated side cross-sectional view of a clamping, cutting and coagulating surgical instrument according to the present invention.

FIG. 1 is an elevated side cross-sectional view of a clamping, cutting and coagulating surgical instrument 10 according to the present invention. Instrument 10 includes a housing 11, an electrically insulative hollow sheath 12 which extends distally from the housing 11, a jaw closure tube 15 extending through the sheath 12, and end effector 14 which extends from the distal end of closure tube 15. End effector 14 includes jaw members 16 and 17. Jaw members 16 and 17 include opposed tissue grasping surfaces 18 and 19 which are arranged to close when closure tube 15 is advanced over camming surfaces 16a and 17a.

Rotatable knob 28 extends from housing 11. Knob 28 engages sheath 12 and closure tube 15 which, in turn, engages jaw members 16 and 17. Knob 28 may be used to rotate jaw members 16 and 17 into position to grasp and clamp tissue. A pivoting handle member 30 is coupled to closure tube 15 and is arranged to rotate about pivot 41 to provide a transitional longitudinal movement to closure tube 15 through linkage 40. Cutting element 22 is actuated by pusher knob 31 which extends from outside housing 11 into closure tube 15 in housing 11. Pusher knob 31 is coupled to drive rod 29 which extends through closure tube 15 and couples on its distal end to the cutting element 22. Spring 32, which is located in closure tube 15, abuts against the distal end of the pusher knob 31 and against the proximal end 27 of jaw members 16 and 17. Spring 32 provides for the automatic retraction of the cutting element 22 when pusher knob 31 is released.

Figure 2:
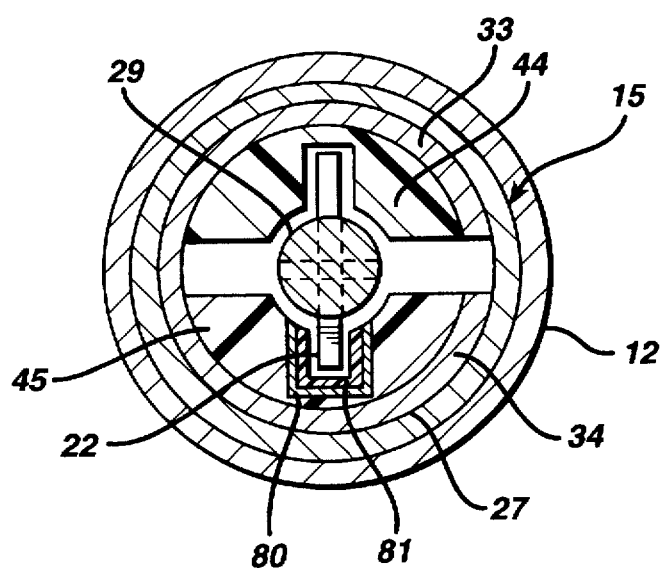
FIG. 2 is cross-section view of the surgical instrument illustrated in FIG. 1 along cutaway A—A.

Generator 35 is an electrosurgical generator capable of providing bipolar energy to the end effector and may be activated by, for example, a user controlled foot switch 36. Generator 35 includes a first output 137a and a second output 137b. When foot switch 36 is closed to actuate generator 35, an electrical potential is developed across outputs 137a and 137b. The frequency of the electrical potential developed by generator 35 is generally within the Radio Frequency or RF range. Wire 37a couples output 137a, through housing 11, to electrical contact 38 on closure tube 15. Wire 37b couples output 137b, through housing 11, to electrically insulated wire 39 which extends through closure tube 15 to inner electrode 80. Electrical current will flow from output 137a to output 137b when a conductive path is provided FIG. 2 is a cross-section view A—A of the surgical instrument illustrated in FIG. 1. In FIG. 2, insulative hollow sheath 12 surrounds electrically conductive closure tube 15. Outer electrodes outer 33 and 34 surround electrically insulative regions 44 and 45 respectively. Inner electrode 80 is surrounded by insulative region 45. Channel insulator 81 is formed to an electrically insulative material and is surrounded by inner electrode 80. Channel insulator 81 forms a channel for cutting element 22. Cutting element 22 is mounted on drive rod 29. Closure tube 15, being electrically conductive, provides an electrical path from electrical contact 38 to outer electrodes 33 and 34. Thus, electrical current may flow from generator output 137a to outer electrodes 33 and 34. Wire 37b and wire 39, being electrically conductive, provide an electrical path from inner contact 80 to generator output 137b.

FIG. 3 is a perspective break away view of end effector 14 of the surgical instrument 10. As illustrated in FIG. 3, jaw members 16 and 17 include channel 20 and channel 21 formed therein to guide cutting element 22 as it is advanced through jaw members 16 and 17. Cutting element 22 includes prongs 23 and 24 which are separated at the distal end of the cutting element 22. The distal end of each prong 23 and 24 is formed into cutting blades 25 and 26, respectively. Blades 25 and 26 ride within channels 20 and 21 respectively as cutting element 22 is advanced through jaw members 16 and 17. Blades 25 and 26 are angled so that when the prongs 23 and 24 overlap, blades 25 and 26 form a V-shaped shearing member. Prongs 23 and 24 comprise springs which tend to separate blades 25 and 26 as the gap between jaw members 16 and 17 increases, for example, in thicker tissues. As the gap increases, the area of overlap decreases.

In FIG. 3, jaw members 16 and 17 include outer electrodes 33 and 34 which are electrically connected to closure tube 15. Electrode 80 is electrically connected to wire 39. Electrodes 33 and 34 form at least a portion of surfaces 18 and 19 respectively. In end effector 14, electrodes 33 and 34 are offset from electrode 80 to avoid electrical shorts between the electrodes when the jaw members are closed.

Electrode 33 and 34 are electrically isolated from electrode 80. Closure tube 15 is constructed of, for example, a conductive metal and contacts the outer electrode 13 of jaw member 16 and outer electrode 34 of jaw member 17. Jaw member 17 further includes region 45 which is formed of an electrically insulative material and is surrounded by outer electrode 34. U-shaped electrode 80 is formed of an electrically conductive material formed on the inside of the insulative region 45. The interior of electrode 34 is lined with insulative material which forms channel insulator 81. Channel insulator 81 forms the lower half 21 of knife channel 43. Top jaw 16 also includes insulative region 44 which is formed of an electrically insulative material on the inside of electrode 33. The interior of insulative region 44 forms the top half 20 of knife channel 43. The distal end of jaw member 16 and 17 has an inwardly angled shape. The inwardly angled distal ends of jaws 16 and 17 forms a V-shaped space which assists in channeling tissue in between jaws 16 and 17. In FIG. 3, jaw member 16 includes a plurality of winged electrodes 61 and jaw member 17 includes a plurality of wing ed electrodes 62.

FIG. 4 is a side view of an end effector including winged electrodes according to the present invention. In FIG. 4, top jaw 16 and bottom jaw 17 are in a spaced apart position arranged to grasp or position tissue therebetween. FIG. 5 is a side view of the end effector illustrated in FIG. 4 with tissue grasped between the jaws of the instrument. In FIG. 5 end effector 14 engages tissue 98 so that tissue 98 may be treated by, for example, applying electrosurgical energy. Once the tissue is treated, knife 22 may be advanced to cut the treated tissue.

Figure 6:
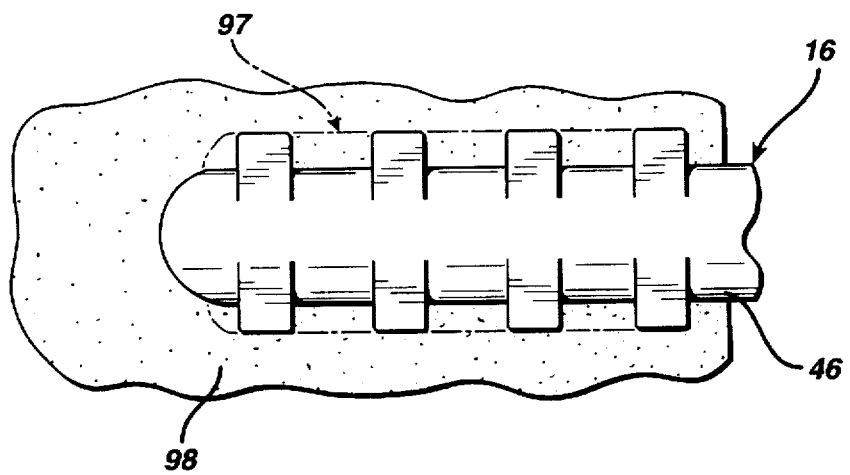
FIG. 6 is a top plan view of the end effector illustrated in FIG. 5 as it is being used to electrosurgically treat engaged tissue.

FIG. 6 is a top plan view of the end effector illustrated in FIG. 5 showing the end effector being used to electrosurgically treat engaged tissue 98. An area of thermal spread in tissue 98 surrounding the end effector is illustrated as region 97. In region 97, desiccation of and/or thermal effects on the tissue may appear as, for example, changes in color or texture of the tissue.

Figure 7:
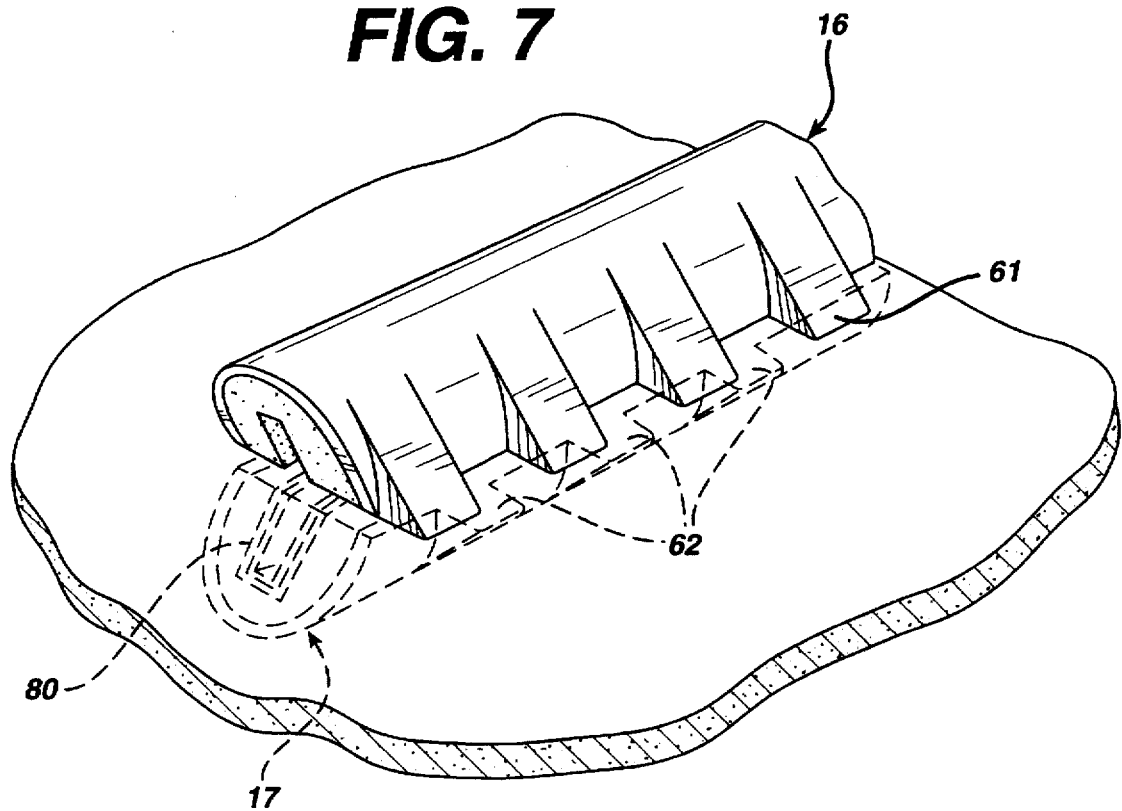
FIG. 7 is a side perspective view of the end effector illustrated in FIG. 6.
Figure 8:
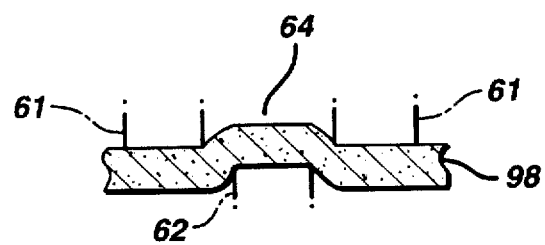
FIG. 8 is a side view of a portion of the end effector illustrated in FIG. 5.

FIG. 7 is a side perspective view of the end effector illustrated in FIG. 8. Jaw 16 includes wing electrodes 61 which contact portions of tissue engaged between jaw 16 and opposing jaw 17. Outer surface 33 of jaw 16 is electrically conductive and provides contact to wing electrode 61. Jaw 17 also includes wing electrode 62 shown on outline which are offset from electrodes 61 and which contact portions of tissue. When electrically conductive tissue is grasped by jaws 16 and 17, electric current will flow from electrode 80 through the tissue to wing electrodes 61 and 62.

FIG. 8 is a side view of a portion of the end effector illustrated in FIG. 5. In FIG. 8, tissue 98 is held between wing electrodes 61 and 62. As FIGS. 5 and 8 illustrate, in one embodiment of the present invention, the wing electrodes 61 and 62 may be arranged on jaws 16 and 17 respectively such that the wing electrodes do not overlap when the instrument is closed. Further, the wing electrodes may be designed as illustrated in FIGS. 5 and 8 such that the center line of the wing electrodes on each jaw are aligned with the center of the gap between electrodes on the opposing jaw. In this embodiment, the width of the wing electrodes on each jaw is slightly smaller than the width of the gap between electrodes on the opposing jaw. For example, in FIG. 8, the center of the gap 64 between wing electrodes 61 is approximately aligned with the center of wing electrode 62 and wing electrode 62 is smaller than gap 64. The winged electrode arrangement illustrated in FIGS. 5 and 8 is advantageous because, by offsetting the winged electrodes, the treated tissue is visible from either side of the end effector. In addition, because the winged electrodes are smaller than the gap on the opposing jaw, the tissue is supported without tearing against the edges of the electrode.

Figure 9:
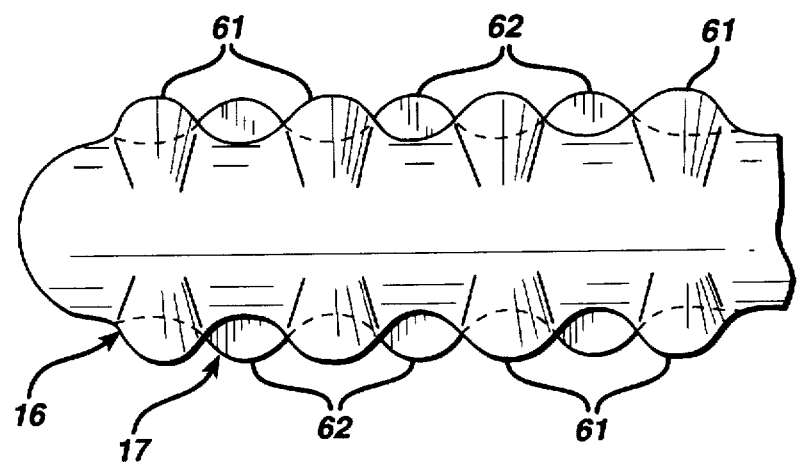
FIG. 9 is a top view of an alternate embodiment of an end effector according to the present invention.

FIG. 9 is a top view of an alternate embodiment of an end effector according to the present invention. In FIG. 9, winged electrodes 61 and 62 are rounded to further reduce the chance that the edges of the winged electrodes will tear tissue grasped by the end effector. In the embodiment of FIG. 9, winged electrodes 61 and 62 are designed to have an atraumatic shape, that is, a shape which does not damage surrounding tissue as the instrument is inserted, retracted and manipulated. Atraumatic shapes for the winged electrodes described herein may include rounded designs such as the winged electrodes illustrated in FIG. 9, angled designs, or beveled designs.

Figure 10:
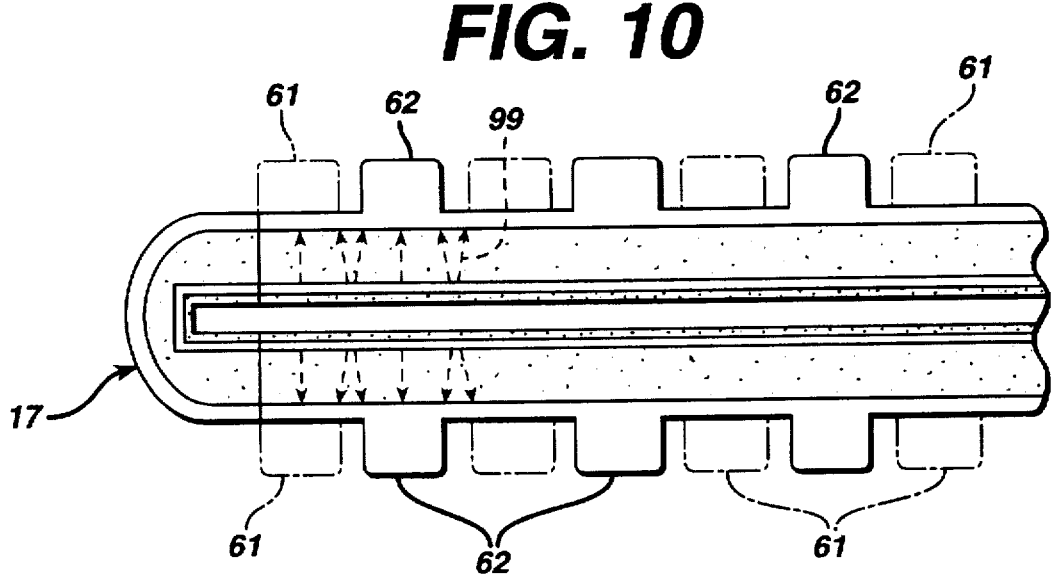
FIG. 10 is a top view of the jaw of the end effector illustrated in FIG. 1.

FIG. 10 is a top view of the jaw of the end effector illustrated in FIG. 1. In FIG. 10, arrows 99 indicate schematically how electrical current flows from electrode 80 through tissue grasped in the end effector to the winged electrodes 61 and 62.

Other embodiments of the present invention may include other types of cutting elements, such as a wire. Alternatively, the present invention may be incorporated into grasping instruments which do not incorporate any type of cutting element, such as a forceps or other grasping or manipulation instrument. The present invention may also be incorporated into instruments which utilize staples, clips or other fixation devices, either alone or in combination with a cutting element such as a knife. The present invention may also be incorporated into articulating instruments. The present invention may also be incorporated into surgical instruments which include curved end effectors. The present invention may also be incorporated into many types of surgical instruments, including endoscopic instruments, laparoscopic instruments, videoscopic instruments and open instruments.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

We claim:

1. An electrosurgical instrument including an end effector operatively connected to said instrument, wherein said end effector comprises:
    first and second tissue grasping surfaces, a portion of said first and said second tissue grasping surfaces overlapping when said end effector is closed, wherein at least one of said first and second tissue grasping surfaces comprise:
        a first electrically conductive electrode; and
        at least one or more electrically conductive wing electrodes wherein said wing electrode forms a portion of and extends laterally from said overlapping portion.

2. An electrosurgical instrument including an end effector operatively connected to said instrument, wherein said end effector comprises:

a first tissue grasping surface;

a second tissue grasping surface wherein a portion of said first grasping surface overlaps a portion of said second grasping surface when said end effector is closed;

a first electrode on said first tissue grasping surface; and at least one electrically conductive wing electrode attached to said first tissue grasping surface and insulated from said first electrode wherein said wing electrode forms a portion of and extends laterally from said overlapping portion of said first tissue grasping surface.

3. The electrosurgical instrument of claim 2 wherein said instrument further comprises:

a cutting element;

a first channel formed in said first grasping surface;

a second channel formed in said second grasping surface;

a mechanism operatively connected to said instrument and said cutting element, wherein said cutting element is moveable within said first and second channels, between said tissue grasping surfaces, to cut tissue positioned between said tissue grasping surfaces.

4. The electrosurgical device of claim 3, wherein each of said first and second tissue grasping surfaces further comprises a proximal and distal portion, and said end effector further comprises a longitudinal axis extending proximal to distal through said end effector; and wherein said cutting element is moveable in a direction from the proximal to distal portions of said surfaces.

5. An electrosurgical instrument including an end effector operatively connected to said instrument, wherein said end effector comprises:

first and second tissue grasping elements;

a first tissue grasping surface on said first element;

a second tissue grasping surface on said second element wherein a portion of said first grasping surface overlaps a portion of said second grasping surface when said end effector is closed;

at least one electrode on one of said tissue grasping surfaces;

at least one wing electrode attached to at least one of said grasping elements wherein said wing electrode forms a portion of and extends laterally from said grasping surface of said at least one grasping element.

6. An electrosurgical instrument according to claim 5 wherein each of said grasping elements includes at least one electrically conductive wing electrode.

7. The electrosurgical instrument of claim 6 wherein said instrument further comprises:

a cutting element;

a first channel formed in said first grasping surface;

a second channel formed in said second grasping surface;

a mechanism operatively connected to said instrument and said cutting element, wherein said cutting element is moveable within said first and second channels, between said tissue grasping surfaces to cut tissue positioned between said tissue grasping surfaces.

8. The electrosurgical device of claim 7, wherein each of said first and second tissue grasping surfaces further comprises a proximal and distal portion, and said end effector further comprises a longitudinal axis extending proximal to distal through said end effector; and wherein said cutting element is moveable in a direction from the proximal to distal portions of said surfaces.

9. An electrosurgical instrument comprising:

a shaft having a distal end and a longitudinal axis;

an end effector operatively connected to said instrument, located at the distal end of the shaft, adapted to receive bipolar energy therein, said end effector comprising:

a distal end; and first and second elements comprising first and second opposed tissue contacting surfaces respectively, said surfaces moveable relative to each other from an open, spaced-apart position for positioning tissue therebetween, to a closed position for grasping the tissue, at least a portion of one of said tissue contacting surfaces comprising a first electrode, and at least a portion of one of said tissue contacting surfaces comprising an electrically isolated second electrode, said first and second elements further comprising first and second outer surfaces, respectively, said first and second outer surfaces adjacent said first and second tissue contacting surfaces, respectively, at least one of said first and second electrodes being contained substantially between said first and second outer surfaces;

wherein at least one of said first and second outer surfaces include at least one winged electrode wherein said winged electrode forms a portion of and extends laterally from said at least one outer surface.

10. An electrosurgical instrument including an end effector operatively connected to said instrument, wherein said end effector comprises:

a first tissue grasping surface;

a second tissue grasping surface wherein a portion of said first grasping surface overlaps a portion of said second grasping surface when said end effector is closed;

a first electrode on said first tissue grasping surface; and at least one electrically conductive wing electrode attached, forming a portion of, and extending laterally from said overlapping portion of said first tissue grasping surface and insulated from said first electrode, wherein said wing electrode has an atraumatic shape.

11. The electrosurgical instrument of claim 10 wherein said wing electrode has a rounded shape.

12. The electrosurgical instrument of claim 11 wherein said instrument further comprises:

a cutting element;

a first channel formed in said first grasping surface;

a second channel formed in said second grasping surface;

a mechanism operatively connected to said instrument and said cutting element, wherein said cutting element is moveable within said first and second channels, between said tissue grasping surfaces, to cut tissue positioned between said tissue grasping surfaces.

* * * * *